United States Patent [19]

Sturtz et al.

[11] 4,200,594

[45] Apr. 29, 1980

[54] 3-(1,6-)DIAMINOHEXYL-DILOWERALKYL) PHOSPHONATES

[76] Inventors: Georges Sturtz, 22, rue Léon Blum, 29200 Brest; Jean-Claude Clement, 76106 Résidence Bois des Roches, 91240 Saint Michel sur Orge, both of France

[21] Appl. No.: 861,948

[22] Filed: Dec. 19, 1977

Related U.S. Application Data

[62] Division of Ser. No. 801,809, May 31, 1977, abandoned, which is a division of Ser. No. 693,686, Jun. 7, 1976, abandoned.

[30] Foreign Application Priority Data

Jun. 10, 1975 [FR] France .................................. 75 18179

[51] Int. Cl.$^2$ ................................................ C07F 9/30
[52] U.S. Cl. ..................................... 260/944; 260/938; 260/940; 260/942; 528/72; 528/287; 528/337; 528/370; 528/399
[58] Field of Search ........................ 260/940, 942, 944

[56] References Cited

U.S. PATENT DOCUMENTS

| 2,668,800 | 9/1951 | Johnston | 260/30.6 |
| 3,812,221 | 5/1974 | Braden | 260/968 |
| 4,029,679 | 6/1977 | Kötzsch | 260/348 R |

*Primary Examiner*—Glennon H. Hollrah
*Assistant Examiner*—Lisa Jones
*Attorney, Agent, or Firm*—Bacon & Thomas

[57] ABSTRACT

This invention concerns the preparation of dinitrile phosphonates, as well as their hydrolysis into the corresponding diacids, and reduction into the corresponding diamines. These compounds can be used, in particular, to make polyamides, polyurethanes or polyurates fireproof, as well as to increase their adhesive properties.

2 Claims, No Drawings

3-(1,6-)DIAMINOHEXYL-DILOWERALKYL) PHOSPHONATES

This is a division of application Ser. No. 801,809, filed May 31, 1977, now abandoned, which in turn is a divisional application of Ser. No. 693,686, filed June 7, 1976, now abandoned.

This invention concerns the preparation of dinitrile phosphonates, as well as their hydrolysis into the corresponding diacids, and reduction into the corresponding diamines. These compounds can be used, in particular, to make polyamides, polyurethanes or polyurates fireproof, as well as to increase their adhesive properties.

Non-reactive fireproofing agents containing phosphorus already exist for macromolecules. However, they tend to exude polymer, and their effects diminish in time. It is therefore better to introduce phosphorus in the form of a comonomer taking part in the copolymerization or copolycondensation reaction.

These new dinitrile phosphates have the following formula:

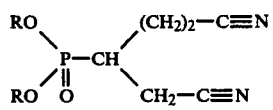

where R is a branched or unbranched alkyl radical containing from 1 to 5 carbon atoms. These products may be obtained by means of the following formula:

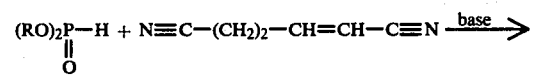

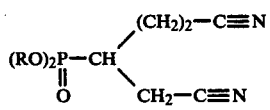

The procedure consists of mixing the dialkyl phosphite 2 with the 1,4-dicyano 1-butene 3 in stoichiometric amounts, then adding some drops of a basic agent (alkaline alcoholate in a saturated alcohol solution, for example) until no further heating occurs. External cooling is required. Distillation is then performed at reduced pressure to obtain satisfactory yields of dinitrile phosphonates 1. Examples of experimental conditions are given below.

The corresponding diamines are obtained by catalytic hydrogenation of the dinitriles of formula 1. One of the problems involved in hydrogenation of dinitriles is the formation alongside the diamine of cyclic secondary amine, in proportions that vary depending on the size of the cycle. This parasitic reaction can usually be minimized by careful choice of catalyst and by using ammonia.

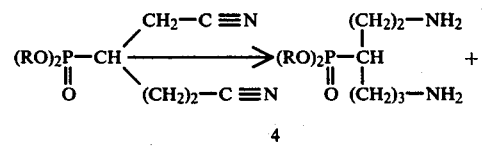

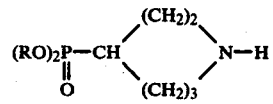

Various hydrogenation catalysts have been tested, the best results being obtained with platinum oxide in a hydrochloric ethanol medium. Sufficiently pure diamine 4 can be obtained, however, using Raney cobalt in a dioxane medium.

The corresponding diacids can be obtained by acid hydrolysis of the dinitriles.

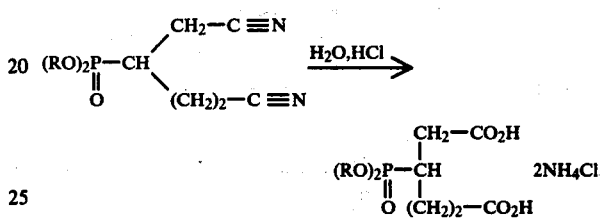

However, it is difficult to obtain selective hydrolysis of the two nitrile functions without partly hydrolysing phosphoric ester functions. Another method can be used, which involves passing by way of the corresponding diamide, and subsequent treatment with nascent nitrous acid, according to the following reaction formula:

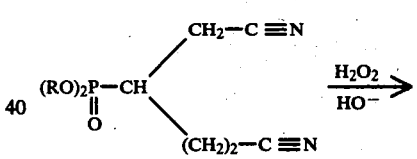

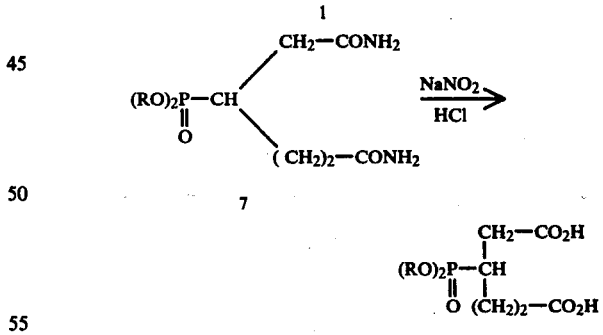

These difunctional compounds can produce polycondensation reactions from difunctional substrates. Polymers can be obtained, for instance, by condensation of diamines 4 with di-isocyanates, according to the formula:

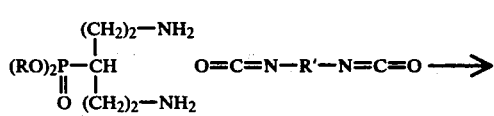

-continued

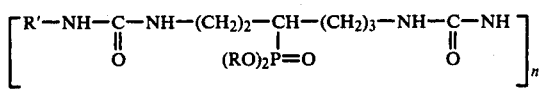

Similarly, diamine phosphonates 4 react with bis-chloroformiates to produce polyurethanes, or with carboxylic diacids to produce polyamides.

The invention is illustrated by, witout being in any way confined to, the following examples.

EXAMPLE 1

A saturated sodium methylate solution was added drop by drop to a mixture of 11 g dimethylphosphite and 10.6 g 1.4-dicyano 1-butane, until no further heating occurred (approximately 15 drops were needed). The mixture was then agitated for 1 hour at atmospheric temperature, and distilled at reduced pressure. This produced 16.57 g (77%) 2-(1.4-dicyano butyl) dimethyl phosphate 1a.

| Analysis | Calculated % | Experimental % |
|---|---|---|
| C | 44.44 | 44.25 |
| H | 6.02 | 6.1 |
| N | 12.96 | 13.03 |
| P | 14.35 | 14.12 |

$n^{17} = 1.4638$
$BP_{0.02} = 172°$ C.
IR: C≡N at 2255 cm$^{-1}$; P=O at 1248 cm$^{-1}$

EXAMPLE 2

A saturated sodium ethylate solution was added drop by drop to a mixture of 42.4 g (0.4 moles) 1.4-dicyano 1-butene and 55.2 g (0.4 moles) diethylphosphite, until no further heating occurred (approximately 25 drops were needed). The mixture was then agitated for 1 hour at atmospheric temperature, and distilled at reduced pressure. This produced 70 g (72%) 2-(1.4-dicyano butyl) diethyl phosphonate 1b.
$BP_{0.01} = 172°$ C.
$n^{17} = 1.4571$

| Analysis | Calculated % | Experimental % |
|---|---|---|
| C | 49.18 | 49.3 |
| H | 6.97 | 7.05 |
| N | 11.47 | 11.31 |
| P | 12.7 | 12.55 |

IR: C≡N at 2255 cm$^{-1}$; P=O at 1245 cm$^{-1}$

EXAMPLE 3

The same operation was performed as in example 2, with 16.6 g di-isopropyl phosphite and 10.6 g 1.4-dicyano 1-butene. This produced 11 g (40%) 2-(1.4-dicyano butyl) di-isopropyl phosphonate 1c.
$BP_{0.01} = 172°$ C.
$n^{17} = 1.4571$

| Analysis | Calculated % | Experimental % |
|---|---|---|
| C | 52.94 | 53.1 |
| H | 7.72 | 7.6 |
| N | 10.29 | 10.05 |
| P | 11.39 | 11.55 |

IR: C≡N at 2255 cm$^{-1}$; P=O at 1248 cm$^{-1}$

EXAMPLE 4

10 g dinitrile phosphonate 1b (described in example 2), 200 ml ammonia-saturated ethanol and 2 g Raney nickel W-2 were placed in a 500 ml autoclave, which was heated to 90° C. for 2 hours at 80 bars hydrogen pressure. After cooling, filtration and evaporation, the amine was analysed by the method of Siggia et coll. (published in *Analytical Chemistry*, 1950, 22, page 1295), with the following results:

Primary amine 4: 40%; Secondary amine 5: 60% and with a temperature of 110° C. and 95 bars pressure:

Primary amine 4: 53%; Secondary amine 5: 47%

EXAMPLE 5

The same operation was performed as in example 4, replacing the nickel with Raney cobalt W-2. The temperature was 110° C., and hydrogen pressure 95 bars. Results were as follows:

Primary amine 4: 90%; Secondary amine 5: 10% and when the ammonia-saturated ethanol was replaced with ammonia-saturated dioxane:

Primary amine 4: 95%; Secondary amine 5: 4.5%

EXAMPLE 6

5 g dinitrile phosphonate 1b, 500 mg platinum oxide, 190 ml ethanol and 5 ml concentrated hydrochloric acid were placed in the autoclave, which was agitated for 14 hours at 25° C. and 70 bars hydrogen pressure. After filtration of the catalyst and elimination of the solvent, water and chloroform were added, obtaining a pH-value of 10 by adding soda. The organic phase was washed several times in water, then dried on sodium sulphate. The chloroform was removed at reduced pressure. Results of analysis were as follows:

Primary amine 4: above 99%; Secondary amine 5: less than 1%

EXAMPLE 7

12.2 g dinitrile phosphate 1b were added drop by drop to a solution of 40 ml water oxygenated to 30 volumes, 55 ml methanol and 4 volumes sodium hydroxide 6 N, keeping the temperature below 35° C. A large amount of oxygen was released. The mixture was then agitated for 1 hour, and the solvent expelled at reduced pressure. The diamide phosphonate 7 was a highly viscous, colourless liquid. Its NMR showed that phosphoric ester functions were not hydrolysed under these conditions. This compound was added directly to a solution of 6.9 g sodium nitrite in 60 ml water, and 10 ml concentrated hydrochloric acid (d=1.19) were added drop by drop, causing nitrogen to be released. The temperature was kept below 30° C. The mixture was agitated for 1 hour, and the water was removed at reduced pressure; the residue was then mixed with acetone. The insoluble part (sodium chloride) was removed by filtration, and the acetone expelled. The NMR spectrum of the resulting diacid 6 showed that the phosphoric ester functions were not hydrolysed, the following signals being recorded (in deuterochloroform, internal reference TMS, δ in ppm):

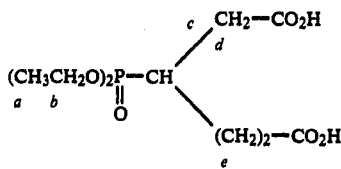

6Ha at 1.3 (triplet); 4 Hb at 4.1 (quintuplet); 2 Hc+Hd+He between 2 and 3 (block); 2 Hf at 11.8 (widened singulet).

EXAMPLE 8

1.74 g (0.01 moles) toluene di-isocyanate dissolved in 25 ml carbon tetrachloride were added slowly to 2.52 g (0.01 moles) diamine phosphonate 4 dissolved in 100 ml carbon tetrachloride, while fast agitation was in progress. The temperature rose from 20° to 45° C. After 5 minutes agitation, precipitation was completed with 200 ml hexane, followed by Buchner funnel filtration and vacuum-drying in a drier. The resulting polyurate was in the form of a white powder $\{\eta\}=0.08$ d/g (in DMF at 30° C.).

EXAMPLE 9

12.6 g (0.05 moles) diamine phosphonate 4, 10.6 g (0.1 moles) sodium carbonate, 1.5 g sodium lauryl sulphonate and 150 ml water were placed in a 500 ml reactor equipped with a vibratory agitator.

The mixture was cooled to 5° C. and 11.55 g (0.05 moles) diethylene glycol bis-chloroformiate in 125 ml benzene were added. After 10 minutes' agitation, the polymer was collected by filtration, and vacuum-dried in a drier. It took the form of a flexible, elastic mass, soluble in chloroform.

The NMR spectrum (CDCl$_3$; δ in ppm, internal reference TMS) was:

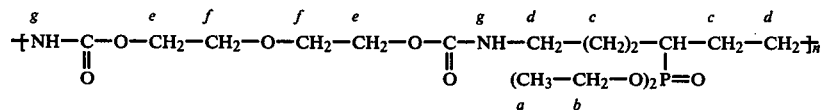

Ha and Hc between 1 and 2 (triplet and block); Hb+He between 3.7 and 4.5 (multiplet); Hd around 3.15 (block); Hf at 3.65 (block); Hg at 5.7 (block).

EXAMPLE 10

A mixture of 2.7 g (containing 0.02 eq NH$_2$ according to analysis) diamine phosphonate 4 and 1.46 g (0.01 moles) adipic acid was heated to 210° C. for 3 hours, in a tube through which a current of nitrogen passed. This produced a hard, brittle, translucent polyamide, soluble in acetic acid.

As previously indicated the diamine phosphonates according to the invention are useful, among others, to prepare fire-proof polymers by reacting said diamines, using the operating conditions of conventional polycondensation processes, with compounds such as:

diisocyanates having the formula O=C=N—R'—N=C=O wherein R' represents a divalent organic radical, in particular a divalent hydrocarbon radical and preferably an aromatic or aliphatic hydrocarbon radical, such as toluylene diisocyanate, hexamethylene diisocyanate, diisocyanodiphenyl methane, phenylene diisocyanate;

bis-chloroformates, in particular alkylene glycol bis-chloroformates or polyalkylene glycol bis-chloroformates, such as diethylene glycol bis-chloroformate, propylene glycol bis-chloroformate, ethylene glycol bis-chloroformate, triethylene glycol bis-chloroformate, butylene glycol bis-chloroformate;

dicarboxylic acids with the formula HOOC—R''—COOH wherein R'' represents a divalent organic radical, in particular a divalent hydrocarbon radical such as a divalent aromatic or aliphatic hydrocarbon radical and preferably a C$_4$ to C$_{20}$ alkylene radical, such as adipic acid and sebacic acid.

The symbol n appearing in some of the precited formulas is an integer representing the number of elementary units in the polymer resulting from the polycondensation reaction.

What is claimed is:

1. A compound of the formula

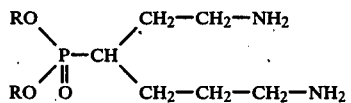

wherein R is a branched or unbranched alkyl containing 1 to 5 carbon atoms.

2. The compound as defined in claim 1 which is 3-(1,6-diaminohexyl)diethylphosphonate.

* * * * *